US010172679B2

(12) United States Patent
Mewes et al.

(10) Patent No.: US 10,172,679 B2
(45) Date of Patent: Jan. 8, 2019

(54) MEDICAL ROBOTIC DEVICE AND METHOD FOR THE OPERATION THEREOF

(71) Applicant: Siemens Healthcare GmbH, Erlangen (DE)

(72) Inventors: Philip Mewes, Nuremberg (DE); Michael Wiets, Langensendelbach (DE)

(73) Assignee: Siemens Healthcare GmbH, Erlangen (DE)

( * ) Notice: Subject to any disclaimer, the term of this patent is extended or adjusted under 35 U.S.C. 154(b) by 119 days.

(21) Appl. No.: 15/366,613

(22) Filed: Dec. 1, 2016

(65) Prior Publication Data
US 2017/0151025 A1 Jun. 1, 2017

(30) Foreign Application Priority Data
Dec. 1, 2015 (DE) .................. 10 2015 223 921

(51) Int. Cl.
*A61B 34/00* (2016.01)
*A61B 34/30* (2016.01)
*A61B 34/10* (2016.01)
*A61B 34/20* (2016.01)
*A61B 5/00* (2006.01)
*A61B 17/17* (2006.01)
(Continued)

(52) U.S. Cl.
CPC ............ *A61B 34/30* (2016.02); *A61B 5/7267* (2013.01); *A61B 17/1757* (2013.01); *A61B 34/10* (2016.02); *A61B 34/20* (2016.02); *A61B 2017/00699* (2013.01); *A61B 2017/00703* (2013.01); *A61B 2034/306* (2016.02); *A61B 2090/064* (2016.02); *A61B 2090/066* (2016.02)

(58) Field of Classification Search
USPC ............................. 700/245–264; 606/1, 130
See application file for complete search history.

(56) References Cited

U.S. PATENT DOCUMENTS 6,594,517 B1 * 7/2003 Nevo ................. A61B 1/00147
128/899
6,837,892 B2 * 1/2005 Shoham ............. A61B 17/1757
606/130
(Continued)

OTHER PUBLICATIONS

CyberKnife® Robotic Radiosugery System: Respiratory Motion Solutions, Accuray brochure (2009).
"Motion Management," Accuray brochure (2014).

*Primary Examiner* — Jonathan L Sample
(74) *Attorney, Agent, or Firm* — Schiff Hardin LLP

(57) ABSTRACT

A medical-robotic device that has a kinematic chain of movable components with an end effector at one end, with at least one force or torque sensor for the detection of at least one force or torque value on the kinematic chain. A control processor that controls the kinematic chain. An additional mechanical component is attached directly to the end effector or one of the movable components so that the additional component can transmit a force external to the device or a torque external to the device to the end effector or the movable component. The control processor determines the force external to the device or the torque external to the device on the basis of the at least one force or torque value detected, and controls the kinematic chain in dependence on the determined force external to the device or the determined torque external to the device, in order to increase the accuracy of the medical-robotic device.

12 Claims, 2 Drawing Sheets

(51) Int. Cl.
*A61B 90/00* (2016.01)
*A61B 17/00* (2006.01)

(56) References Cited

U.S. PATENT DOCUMENTS

| | | | |
|---|---|---|---|
| 9,060,678 B2* | 6/2015 | Larkin | A61B 1/00087 |
| 9,333,042 B2* | 5/2016 | Diolaiti | A61B 90/37 |
| 10,028,789 B2* | 7/2018 | Quaid | A61B 17/1764 |
| 2006/0089633 A1* | 4/2006 | L. Bleich | A61B 17/1659 |
| | | | 606/32 |
| 2007/0013336 A1* | 1/2007 | Nowlin | B25J 9/1682 |
| | | | 318/568.21 |
| 2007/0120512 A1* | 5/2007 | Albu-Schaffer | B25J 9/1633 |
| | | | 318/568.2 |
| 2008/0046122 A1* | 2/2008 | Manzo | A61B 1/00149 |
| | | | 700/245 |
| 2008/0307630 A1* | 12/2008 | Hasegawa | B21D 19/043 |
| | | | 29/509 |
| 2009/0088774 A1* | 4/2009 | Swarup | A61B 34/37 |
| | | | 606/130 |
| 2011/0160570 A1* | 6/2011 | Kariv | A61B 5/721 |
| | | | 600/424 |
| 2014/0228631 A1* | 8/2014 | Kwak | A61B 19/2203 |
| | | | 600/102 |
| 2014/0336669 A1* | 11/2014 | Park | A61B 19/2203 |
| | | | 606/130 |
| 2014/0379130 A1* | 12/2014 | Lee | B62D 1/02 |
| | | | 700/259 |
| 2015/0018841 A1* | 1/2015 | Seo | A61B 19/2203 |
| | | | 606/130 |
| 2015/0038980 A1* | 2/2015 | Merscher | A61B 19/2203 |
| | | | 606/130 |
| 2015/0157191 A1* | 6/2015 | Phee | B25J 9/1674 |
| | | | 600/106 |
| 2016/0000512 A1* | 1/2016 | Gombert | A61B 19/2203 |
| | | | 606/130 |
| 2016/0030117 A1* | 2/2016 | Mewes | A61B 19/2203 |
| | | | 600/424 |
| 2016/0030240 A1* | 2/2016 | Gonenc | G01L 5/226 |
| | | | 604/95.01 |

* cited by examiner

MEDICAL ROBOTIC DEVICE AND METHOD FOR THE OPERATION THEREOF

BACKGROUND OF THE INVENTION

Field of the Invention

The invention concerns a medical-robotic device with a kinematic chain of movable components, wherein the kinematic chain has an end effector at its movable end, and with at least one force or torque sensor for the detection of at least one force or torque value on the kinematic chain and with a control processor that controls the kinematic chain. The invention also relates to a method for operating a medical-robotic device of this type.

Description of the Prior Art

In the field of robotic-surgical interventions, which can be performed both for diagnostic and therapeutic reasons, there is also a requirement to achieve the greatest possible accuracy. A major challenge is the compensation of movements on the part of the patient, for example respiratory or cardiac movements, which can greatly impair the accuracy of treatment or diagnosis performed with a medical-robotic device. To achieve such movement compensation, it is initially necessary to detect the movements of the patient, or the patient's anatomy or predetermined anatomical features, relevant for the planned or upcoming intervention. This can take place in real time, but it is alternatively possible for the movements to be recorded and from this recording, a model is calculated to be used as the basis for movement compensation.

A variety of technical approaches to achieve increased accuracy by the use of movement compensation have become established. One example of a product for movement compensation of this type is the "Cyberknife" made by the company Accuray. This uses an external optical tracking system with which movements are optically detected contact-free. Also known are external electromagnetic tracking systems, for example made by the manufacturers Ascension and NDI. In this case, the external trackers are attached to the exterior of the patient and then located by contact-free means over a period of time specified in advance. Here, "external" refers to components that do not belong to a medical-robotic device with which the robotic-surgical intervention is actuated. Hence, such tracking systems are embodied as additional devices with their own housing, which exchange data with the medical-robotic device.

DE 10 2013 002 818 A1 discloses a device for holding a surgical instrument that is designed to be introduced through a sheath into the body of the patient. In this case, each movement of the holder device in both the longitudinal direction and the direction of rotation has the result that the sheath or trocar sleeve moves with respect to the surrounding tissue. To compensate axial movements, a holder for the sheath is arranged on a fixed guide. This enables an axial movement transmitted from the head to the trocar sleeve to be partially or completely compensated. It is also possible for rotational movements of the robotic head to be partially or completely compensated, since the trocar sleeve fan can be rotated around its longitudinal axis by a drive unit.

DE 10 2005 054 575 B3 discloses a method for controlling a robot arm in medical applications with a which a torque acting in at least one joint is detected and controlled by a control device so as to become substantially zero.

SUMMARY OF THE INVENTION

An object of the invention is to increase the achievable accuracy of a medical-robotic device, in particular for a robotic-surgical intervention.

The invention concerns a medical-robotic device with a kinematic chain of movable components, wherein the kinematic chain has an end effector at the movable end. The end effector can be a functionally specific, in particular a medical, end effector. The end effector can also be embodied as a terminal element of the kinematic chain. However, the end effector is preferably attached to a terminal element of the kinematic chain, in particular in a non-destructive reversible manner, for example as a replacement element. The kinematic chain can also have one or more branches with respective further ends. The medical-robotic device can be designed for a robotic-surgical intervention.

The medical-robotic device has at least one force or torque sensor for the detection of a force or torque value on the kinematic chain. At least one force or torque value can be detected for each force or torque sensor. In this case, the force or torque sensors can at least partially, i.e. partially or completely, be arranged on the kinematic chain. They can also be arranged at least partially in the kinematic chain, i.e. within the respective housing of the movable components. The force or torque values emit electrical signals that represent respective forces or torques acting on the movable components.

The medical-robotic device also has a control processor that is configured to control the kinematic chain, and to control the end effector. This control can be effected in dependence on the force or torque values detected.

An essential feature of the invention is an additional mechanical component, which is attached directly to the end effector or one of the movable components of the kinematic chain. In this context, 'directly' should be understood as meaning with no intervening component. The additional component thus can be attached to the end effector independently of the kinematic chain or to the movable component independently of the rest of the kinematic chain. This additional component can be a measuring finger or a measuring probe. The additional component can have an adjustable variable rigidity that enables it to be adapted to different conditions. Therefore, the additional component can be configured in different ways. In particular, the additional mechanical component can be brought into at least one predetermined relative position, preferably two or more predetermined positions, with respect to the end effector and, fixed in the predetermined relative position or positions. In this case, the additional component is preferably attached to the outside of the end effector or the movable component, for example on an outer side of a housing of the end effector or the movable component.

The additional component can also be a further kinematic chain of further movable components.

The additional component transmits a force external to the device or a torque external to the device to the end effector or the movable component. The force external to the device or the torque external to the device can also be transmitted to the end effector when the additional component is attached to the movable component of the kinematic chain. In this case, a force external to the device or a torque external to the device should be understood to be a force or a torque that can be transmitted from an object that is not part of the medical-robotic device, for example a patient or a part of the patient, to the end effector via the additional mechanical component as a coupling element. Therefore, the cause of a force external to the device or a torque external to the device is not attributable to the movement of the device.

In this context, the transmission of the force external to the device or the torque external to the device takes place independently of any other configuration of the end effector. The transmission can take place in one or more preferential directions. In this context, the transmission takes place in precisely one preferential direction. To this end, the additional mechanical component can be specially adapted for force transmission in the preferential direction or preferential directions. For example, this can be effected by a geometric configuration of the additional component with which forces in non-preferential directions are diverted by the additional component and not transmitted. For example, this can be accomplished by the use of a plate oriented in the preferential direction, or another design by which objects transmitting forces or torques to the additional component in non-preferential directions are displaced more easily.

Hence, the fact that the additional component can transmit a force external to the device or a torque external to the device to the end effector also enables a movement of an object that does not belong to the robotic device, for example a patient, to be transmitted to the end effector (and hence also to the kinematic chain). The ability of the additional component to transmit a force external to the device or a torque external to the device to the movable component enables a movement of an object that does not belong to the robotic device, for example a patient, also to be transmitted to the kinematic chain (and hence also to the end effector). This enables the accuracy of the medical-robotic device to be improved not only by a more accurate adjustment of the end effector relative to the object, but also, as explained below, by movement compensation.

It is also essential for the invention for the control processor to be configured to determine the force external to the device or the torque external to the device on the basis of the at least one force or torque value detected, and to control the kinematic chain in dependence on the force external to the device, or the torque external to the device, determined in such a manner.

The invention thus extends the end effector or a movable component of the kinematic chain of the medical-robotic device by an additional mechanical component, which can be brought into mechanical contact with the patient or a part of the patient independently of the position and intended purpose or use of the end effector. At that contact location, the additional mechanical component serves as a sensor that detects at least one of force and torque, for example for accurate positioning of the end effector relative to the stationary object or the moving object (movement compensation). The fact that the additional mechanical component can be positioned independently of the end effector also enables the additional mechanical component to absorb movements, for example of a patient, independently of the end effector and hence to serve as a sensor appliance or detector for movement compensation by the medical-robotic device.

This has the advantage that the accuracy of the medical-robotic device can be increased in a simple, inexpensive way and, for example, that movement compensation can be performed. This increases both the safety and comfort of the patient. In particular in the field of spinal surgery, increased accuracy results in significantly fewer complications and is hence particularly advantageous. It is precisely in such cases that a slight deviation from the optimal drilling path, for example a pedicle screw placement, can result in further instability of a vertebral body that is intact, and hence in post-surgical pain, and make additional operations necessary. Too large a deviation toward the nerve canal can result in damage to the nerve canal and hence in pain or paralysis or even paraplegia. Drilling too deeply in the direction of the abdominal cavity can result in damage to the vena cava or the aorta and hence in death of the patient. Avoiding these potential sources of error increases the safety of the intervention and, as a result of the increased accuracy that is independent of the effort or skill on the part of the surgeon, also enables treatment to be performed more quickly. Hence, rapid amortization of the additional costs for the medical-robotic device can be expected.

In addition, further advantages are obtained compared to optical detection of movement. For example, the possibility of an optical tracker being covered by fluids such as blood, and hence of a result being falsified, is avoided. Also prevented is the possibility of a tracker being covered in some other way, for example, by a surgeon. Also excluded with the present medical-robotic device is the possibility of a change to a geometric thickness (and hence to dimensions of the object) and/or a weight, due to the application of fluid or soft-tissue displacement.

In an embodiment, the additional mechanical component has a fixable slide mechanism and/or at least one fixable joint. The additional component can also be reversibly detachable in a non-destructive manner, for example as a modular replacement element. This means the additional component is more adaptable to different conditions. In particular, the additional component is reversibly detachable without the use of tools. This has the advantage that a number of predetermined relative positions of the additional component with respect to the end effector can be set in a simple manner. For example, a movement of the patient can be detected in a number of relative positions with respect to the end effector, and consequently in a number of different medical situations.

In another embodiment, the additional component has an attachment mechanism that establishes a connection with the object, in particular with a bone of the patient that is maintained solely by friction, sometimes called a force-locked connection. The attachment mechanism can be a screw terminal or the like. This has the advantage that the forces or torques external to the device can be detected particularly accurately, and that not only can compressive forces be transmitted in a specific direction, but also tensile forces can be transmitted in the corresponding opposite direction by the additional component to the end effector.

In a further embodiment, the medical-robotic device has multiple force or torque sensors and the force or torque sensors are arranged at least partially on the kinematic chain. The force or torque sensors can also be integrated in the kinematic chain, preferably in joints of the kinematic chain. Sensors of this kind are known as "integrated torque sensors" made by Kuka Leichtbaurobotern. In this case, the kinematic chain acts both as an actuator for intervention and simultaneously as sensor and actuator for the compensation of forces or torques external to the device. The end effector used for the diagnostic and/or therapeutic intervention is hence used simultaneously, possibly in conjunction with the kinematic chain, as a sensor for movement compensation. Since in its function as a sensor for compensation of forces external to the device, the end effector must be in mechanical contact with the object to which the forces external to the device can be attributed, but in its function as a medical-robotic device for performing the intervention, it does not require mechanical contact, the additional mechanical component closes the remaining gap of the force transmission. Hence, sensors and actuators for the movement compensation and actuators for the intervention are integrated in a single medical-robotic device.

This has the advantage that no additional system external to the device is required for the sensors for movement compensation. This can save costs and space, and avoid visibility problems, since the surgical construction only requires a single device for the intervention and for the movement compensation.

In another embodiment, the at least one force or torque sensor, or in the case of multiple force or torque sensors, one of the force or torque sensors, is part of the additional component. This force or torque sensor is able to detect the force external to the device transmitted by the additional component or the torque external to the device transmitted by the additional component, independently of other forces acting on the kinematic chain, in particular on the end effector. In this case, the other forces exerting an action can be forces that occur as the result of control commands by an operator during the intervention by a movement of the kinematic chain. This has the advantage that the influence of the movements of the patient on the forces detected can be better isolated from the influence of an operator on the forces detected and hence particularly accurate movement compensation can be achieved.

In a further preferred embodiment, the control processor is configured to control the kinematic chain in dependence on the force external to the device determined or the torque external to the device determined such that the magnitude of the force external to the device determined or the magnitude of the torque external to the device determined is kept within a predetermined range of values, in particular minimized, by the end effector being moved in the direction of the determined force external to the device, or in the direction of the determined torque external to the device. In this case, the end effector can be exclusively moved in this direction; in this case, the end effector is exclusively moved with a translatory movement. The direction of the force external to the device determined or the torque external to the device determined can coincide with the preferential direction. This has the advantage that movement compensation is achieved in a particularly efficient manner. In this case, the fact that the end effector is moved in the direction of the determined force external to the device or the determined torque external to the device, means that a relative position of the end effector with respect to the object external to the device responsible for the force external to the device or the torque external to the device is retained unchanged so that particularly high accuracy of movement compensation is achieved. This applies for an exclusive movement in the direction of the determined force or the determined torque.

Hence, the measurement of the movement and the subsequent compensation can take place in all three spatial directions, but at least in one direction, for example the predominant direction of extension of the end effector or the principal axis or predominant direction of extension of an instrument on the end effector, for example a drill sleeve.

In a further embodiment, the control processor is configured to operate in a learning operating mode over a period of time specified in advance, so as to determine the profile of at least one force external to the device or the at least one torque external to the device, and to subsequently operate in a further operating mode, to control the kinematic chain in dependence on the determined profile. This has the advantage that, in the learning operating mode, regardless of any falsification that may occur during the intervention, a model for the profile of the force external to the device or the torque external to the device and hence a movement of the object or the patient can be determined without falsifying influences for an intervention or a treatment. This prevents a specific intervention influencing the accuracy of the movement compensation and hence improves the movement compensation.

In another embodiment, the control processor is configured, in the further operating mode, to control the kinematic chain in dependence on only at least one partial aspect of the determined force external to the device or the determined torque external to the device. For example, the control processor can be configured, in the further operating mode, to control the kinematic chain in dependence on the determined profile and a phase of the determined force external to the device, or the determined torque external to the device, but independently of the magnitude or the size of determined force external to the device or the determined torque external to the device. Alternatively, the control processor can be configured, in the further operating mode, to control the kinematic chain in dependence on the determined profile without taking account of, or without detecting, a further profile or further values of the force external to the device or the torque external to the device.

Hence, the information obtained in the learning operating mode can be used either by itself to compensate a force external to the device or a torque external to the device in the further operating mode, or in combination only with pieces of information obtained in the further operating mode. In both cases, the influence or falsification by the treatment or the intervention is reduced and hence the accuracy of the compensation is increased.

In a further embodiment, the end effector has a drill sleeve with a predominant direction of extension or direction of guidance deviating from an expected direction of the force external to the device or the torque external to the device. The predominant direction of extension or direction of guidance can deviate from the preferential direction of the additional component. It is precisely in such cases that compensation of a movement external to the device responsible for the force external to the device or the torque external to the device is advantageous, since this prevents displacement of the drill sleeve and any corresponding inaccuracy.

The invention also concerns a method for operating a medical-robotic device, wherein the device has a kinematic chain of movable components comprising at one end an end effector. In this case, a first step is the establishment of a mechanical contact between an object and an additional mechanical component, which is attached directly to the end effector or directly to one of the movable components. This object is not part of the device, but is a patient, or a part of a patient, for example a bone. A further step is the transmission of a force external to the device or a torque external to the device by the additional component from the object to the end effector or the movable component. This can be effected by a movement of the object. In this case, the transmission takes place independently of the configuration of the end effector. A next step is the detection of at least one force or torque value on the kinematic chain by at least one force or torque sensor of the medical-robotic device. This is followed by the determination of the force external to the device or the torque external to the device on the basis of the at least one force and torque value detected by a control processor of the medical-robotic device. Finally, the kinematic chain is controlled in dependence on the force external to the device determined or the torque external to the device determined by the control processor. In this case, a movement of the object relative to the end effector or the kinematic chain can be compensated and/or, in the case of a stationary object, a particularly accurate adjustment of the end effector with respect to the object can be achieved by the control.

Advantages and embodiments of the method correspond to advantages and embodiments of the medical-robotic device.

The features and feature combinations cited above in the description and the features mentioned below in the description of the figures and/or shown in the figures alone are usable not only in the respectively specified combinations, but also in other combinations without departing from the scope of the invention. Hence, embodiments of the invention that are not explicitly shown and explained in the figures but are derived from separated feature combinations from the embodiments explained and may be generated thereby are also considered as within the scope of the invention.

DESCRIPTION OF THE PREFERRED EMBODIMENTS

In the figures, the same elements or elements with the same functions are given the same reference numbers.

Figure 1:
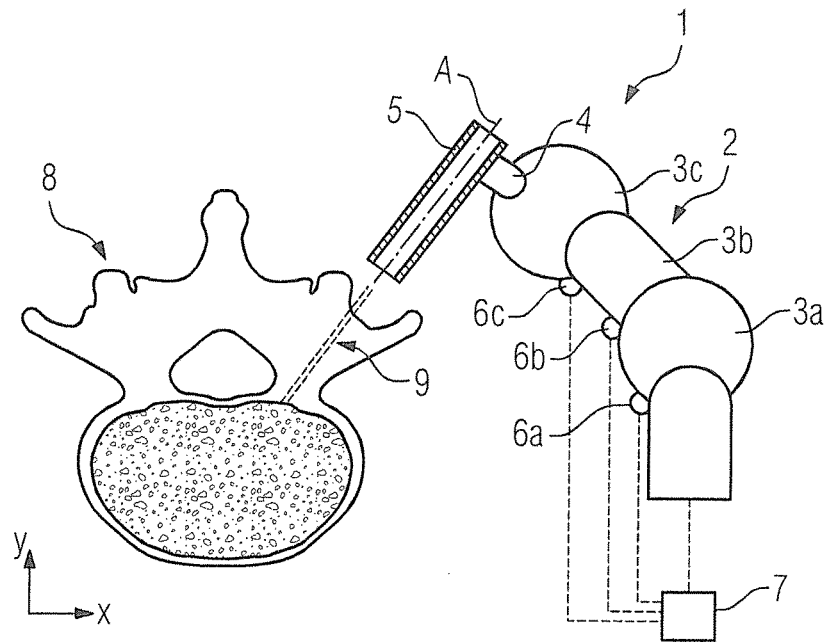
FIG. 1 shows a medical-robotic device according to the prior art in an exemplary application.

FIG. 1 shows a medical-robotic device according to the prior art in an exemplary application. This shows a medical-robotic device 1 with a kinematic chain 2 with movable components 3a, 3b, 3c. In this case, the kinematic chain 2 comprises an end effector 4, which in this example comprises a drill sleeve 5. In this case, the drill sleeve 5 predominantly extends along a guide axis A, which in the present case extends in parallel to the predominant direction of extension of the drill sleeve 5. In the example shown, the robotic device also has a plurality, in this case three, force or torque sensors 6a, 6b, 6c coupled to a control processor 7. The kinematic chain 2 can be controlled by the control processor 7.

The example shown refers to the field of spinal surgery, but is not restricted to this field of application. In spinal surgery, so-called pedicle screws are screwed into the vertebrae to stabilize the spine and connected to rodding. To this end, a desired position 9 of a pedicle screw is initially determined on a radiological image of a vertebra. In this case, the vertebra corresponds to the object 8. Then a hole for the pedicle screw is drilled in the desired position 9. Then, in a further step, the pedicle screw is screwed in. With this type of intervention, a medical-robotic device 1 can assist with accurate positioning of the screws, for example by holding the drill sleeve 5 in a predetermined position relative to the object 8 or relative to the desired position 9 of the pedicle screw.

For the correct positioning of the screws, in the example, the desired position 9 of the pedicle screw is then determined and the medical-robotic device registered to the object 8, i.e. in they are brought into a unique spatial relationship to one another. The drill sleeve 5 is then robotically aligned such that an extension of a guide axis A of the drill sleeve 5 passes through the desired position 9 so that a screw guided through the drill sleeve 5 or a drill guided through the drill sleeve 5 drill can be drilled or screwed into the vertebra according to the desired position 9. During this, in the present case, the position 9 can only pass through the actual vertebral bone, i.e. it must not protrude into the vertebral canal and also must not come too close to a marginal region of the vertebral bone.

However, during this, every movement of the object 8 represents a challenge for the correct positioning of the screws. In the example of the spinal column, the movement can be caused, for example, by patient's respiration or by forces exerted on the patient or vertebra during the intervention by the surgeon and instruments used.

Figure 2:
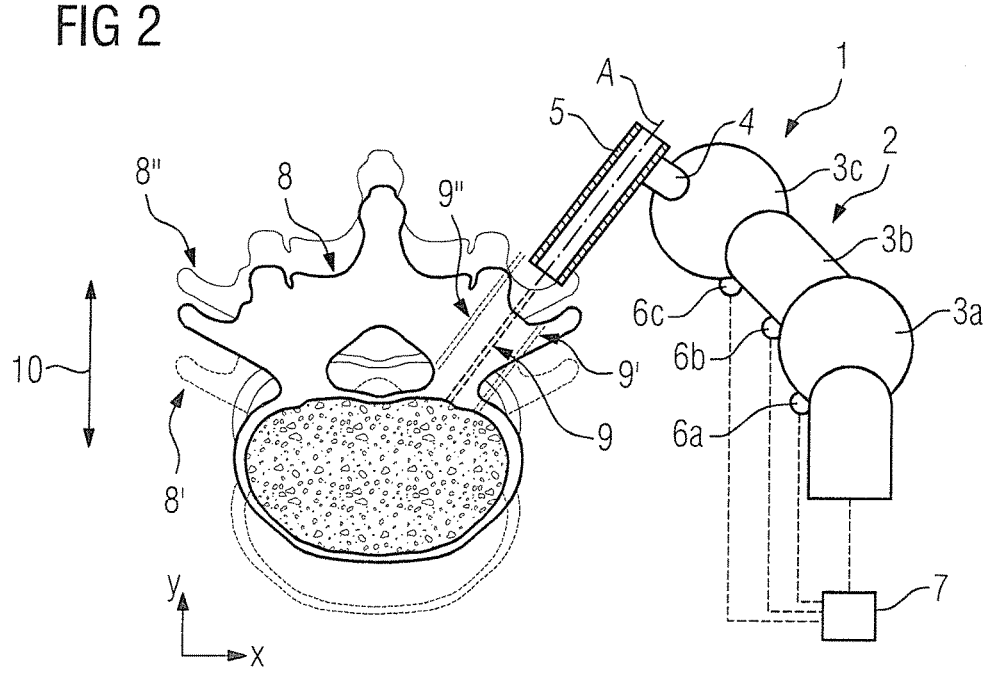
FIG. 2 shows the medical-robotic device of FIG. 1 with a moving patient.

FIG. 2 shows the situation from FIG. 1 with a moving patient. Since the patient and hence also the object 8, in the present case the vertebra, is, for example, moving up and down in the y direction, the object 8 is displaced in accordance with this movement 10. In the example shown, the patient's movement 10 is one-dimensional in the y direction. However, the movement 10 can also be a multi-dimensional movement and/or take place in several spatial directions. With the displaced object 8', 8", the original, registered position 9 now has to be displaced into a different position 9', 9" relative to the end effector 4, i.e. the movement has to be compensated, in order to treat the vertebra at the desired position. Without compensation of the displacement, therefore, in this example, there can be a deviation from the optimum drilling path of the pedicle screw placement. This could cause, for example, an intact vertebral body to be damaged or a nerve in the vertebral canal to be injured. This could also cause injuries to veins and arteries and this can have serious consequences, including the death of the patient.

Figure 3:
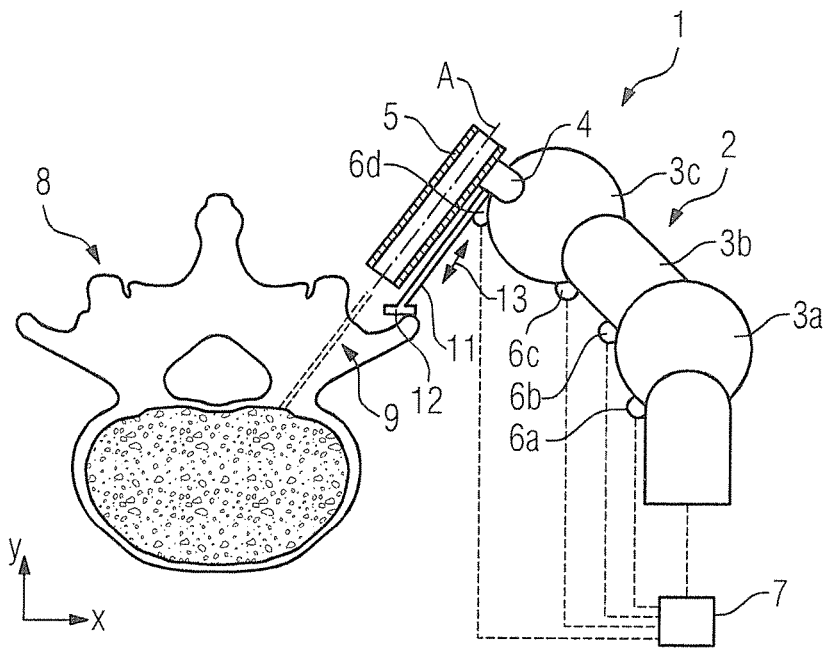
FIG. 3 shows an exemplary embodiment of a medical-robotic device according to the invention similar to the example shown in FIG. 1.

FIG. 3 shows an exemplary embodiment of a medical-robotic device according to the invention. As is known from the prior art, the medical-robotic device 1 has a kinematic chain 2 of movable components 3a, 3b, 3c with an end effector 4. In the present case, there is also a number of force or torque sensors 6a, 6b, 6c arranged on the kinematic chain and a control processor 7 to control the kinematic chain 2. Here, once again the end effector 4 has a drill sleeve 5 with a guide axis A.

In addition, an additional mechanical component 11 is attached to the end effector 4. In the present case, this is a plate 12 which makes the additional component 11 particularly suitable for the transmission of forces from a preferential direction to the end effector 4. In the depiction shown, the plate 12 is oriented parallel to an x-axis and correspondingly is able to absorb forces in the y direction particularly efficiently. The length or orientation of the additional mechanical component 11 can be adapted so that, in the present case, the additional component 11, in the present case especially the plate 12, can be brought into a number of predetermined relative positions with respect to the end effector 4 and hence with respect to the object 8 and can be fixed there. This can be achieved by fixable joints or displacement elements. In the example shown, the length of the additional component 11 can be adapted in accordance with the double arrow 13 parallel to the guide axis A, for example by a telescopic extension element.

This adaptation can establish a mechanical contact between the vertebra as an object 8 external to the object and the device 1. As a result, in the present case, a movement of the object 8 in the y direction results in the transmission of force to the end effector 4. The transmitted force external to the device can be detected by the force or torque sensors 6a-c. In addition, in the present case, a further force sensor 6d is also arranged on the additional component 11 by means of which the force external to the device or a torque external to the device acting on the additional component 11 can be detected independently of another force, for example caused by the intervention, acting on the end effector 4 or the drill sleeve 5. Accordingly, in this case, this enables the control processor 7 to compensate the force external to the device or the movement of the object 8 corresponding to the force more efficiently.

Figure 4:
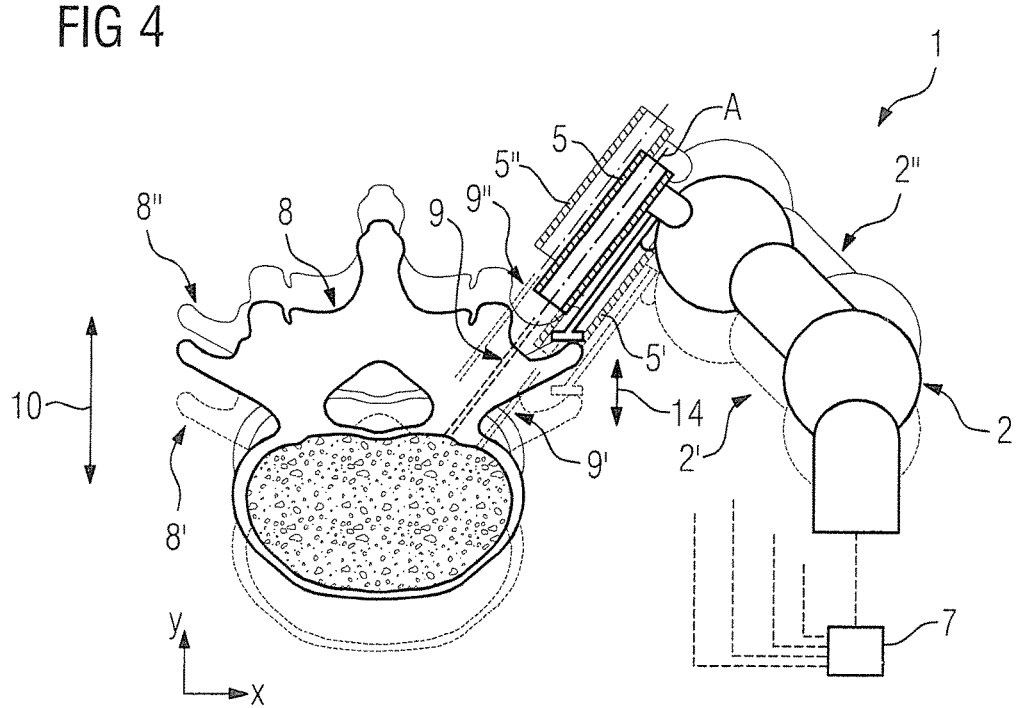
FIG. 4 shows the medical-robotic device shown in FIG. 3 with a moving patient.

FIG. 4 shows similarly to FIG. 2, the medical-robotic device from FIG. 3 with a moving object 8. As an example, here once again a movement 10, symbolized as a large double arrow, is assumed with which the object 8, i.e. the vertebra, rises and sinks rhythmically in one direction. A force external to the device 14 corresponding to this movement is transmitted by the additional mechanical component 11 to the sensors 6a, 6b, 6c, 6d of the robotic device 1. The force external to the device can also act in several spatial directions corresponding to the movement. Correspondingly, in the present case the control processor 7 can keep the force external to the device 14, symbolized by the small double arrow, within a predetermined range of values or minimize that force by the control processor 7 guiding the end effector 4 in the direction of the force external to the device 14. As a result, the kinematic chain 2 moves in accordance with the positions 8', 8" of the object 8 into corresponding positions 2' or 2". Hence, the relative position of the drill sleeve 5, 5', 5" with respect to the desired position 9, 9', 9" is retained. Hence, this enables the movement 10 of the patient, for example a respiratory movement, to be compensated.

In order in this case, despite the presence of the optimization of the additional component 11 to the transmission of a force external to the device 14 exerted in the positive y direction, to also perform movement compensation in the negative y direction, it is possible for the control processor 7 to be adapted always to control the kinematic chain 2 such that the force external to the device 14 has a predetermined magnitude that is very little different from zero. If the object 8 then sinks in the negative y direction, the additional component 11 is relieved, the magnitude of the force external to the device 14 sinks to zero and the kinematic chain 2, and hence the end effector 4 or the drill sleeve 5, is guided in the negative y direction. Alternatively, in this case, the additional mechanical component 11 can be attached to the object 8, for example with a clamping device.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A medical-robotic apparatus comprising:
a kinematic chain comprised of a plurality of movable components, said kinematic chain comprising an end effector at a movable end of said kinematic chain;
at least one kinematic chain sensor, selected from the group consisting of force sensors and torque sensors, that detects, as a sensed value, at least one value experienced by at least one of said movable components, said at least one value being selected from the group consisting of a force value and a torque value;
a control processor that receives said at least one sensed value from said at least one kinematic chain sensor and that is configured to control said kinematic chain using said sensed value detected by said at least one kinematic chain sensor so as to position said end effector at a position that has a spatial relation, determined by said control processor, to an object that is external to said kinematic chain;
a mechanical component having a first end attached directly to an attachment site selected from the group consisting of said end effector and one of said movable components, and having an opposite second end that is adapted for unfixed, touching contact with said object when said end effector is at said position relative to the object, so that said second end is positioned relative to said object independently of said end effector, said mechanical component transmitting a force or torque originating from said object, due to movement of the object, to said attachment site;
a mechanical component sensor, selected from the group consisting of force sensors and torque sensors, that detects, as a further sensed value, at least one value selected from the group consisting of a force value originating from said object and a torque value originating from said object; and
said control processor being configured to receive said further sensed value from said mechanical component sensor and being configured to determine said force or torque originating from said object therefrom, and to augment said control of said kinematic chain dependent on said force or torque originating from said object, so as to maintain said end effector in said spatial relation despite the movement of the object.

2. A medical-robotic apparatus as claimed in claim 1 wherein said mechanical component is at least one mechanical component selected from the group consisting of a fixable displacement mechanism and a fixable joint.

3. A medical-robotic apparatus as claimed in claim 1 wherein said mechanical component comprises an attachment mechanism that attaches said first end of said mechanical component to said attachment site solely by frictional engagement of said first end with said attachment site.

4. A medical-robotic apparatus as claimed in claim 1 comprising a plurality of kinematic chain sensors, selected from said group consisting of force sensors and torque sensors, that each detect a value of a force or torque of said kinematic chain, said plurality of sensors being situated on said kinematic chain.

5. A medical-robotic apparatus as claimed in claim 4 wherein said plurality of kinematic chain sensors are situated respectively in joints of said kinematic chain.

6. A medical-robotic apparatus as claimed in claim 1 wherein said control processor is configured to determine a magnitude of said force or torque originating from the object and to control said kinematic chain dependent on said magnitude of said force or torque originating from the object by keeping said magnitude within a predetermined magnitude range and to operate said kinematic chain to cause said attachment site to be moved in a direction of said force or torque originating from the object.

7. A medical-robotic apparatus as claimed in claim 6 wherein said control processor is configured to keep said magnitude within said predetermined magnitude range by minimizing said magnitude.

8. A medical-robotic apparatus as claimed in claim 1 wherein said control processor is configured to operate in a learning mode over a predetermined time duration in which a time profile of said force or torque originating from the object is determined in said control processor and wherein said control processor is configured to operate in an operating mode, after operating in said learning mode, to control said kinematic chain dependent on said time profile of said force or torque originating from the object determined in said learning mode.

9. A medical-robotic apparatus as claimed in claim 8 wherein said control processor is configured to operate in a further operating mode in which said control processor controls said kinematic chain dependent on only one attribute of said force or torque originating from the object dependent on said time profile determined in said learning mode without using or detecting a further profile or further values of said force or torque originating from the object.

10. A medical-robotic apparatus as claimed in claim 9 wherein said attribute is a phase of said force or torque originating from the object.

11. A medical-robotic apparatus as claimed in claim 1 wherein said end effector is a drill sleeve having a predominate direction of extension that deviates from an expected direction of said force or torque originating from the object.

12. A method for operating a medical-robotic apparatus comprising a kinematic chain of movable components with an end effector at a movable end of said kinematic chain, said method comprising:

with at least one kinematic chain sensor, selected from the group consisting of force sensors and torque sensors, detecting, as a sensed value, at least one value experienced by at least one of said movable components, said at least one value being selected from the group consisting of a force value and a torque value;

providing said at least one sensed value from said at least one kinematic chain sensor to a control processor and, with said control processor, controlling said kinematic chain using said sensed value detected by said at least one kinematic chain sensor so as to position said end effector at a position that has a spatial relation, determined by said control processor, to an object that is external to said kinematic chain;

placing a second end of a mechanical component, having a first end attached directly to an attachment site selected from the group consisting of said end effector and one of said movable components, in unfixed, touching contact with said object when said end effector is at said position relative to the object, so that said second end is positioned relative to said object independently of said end effector, and from said mechanical component, transmitting a force or torque originating from said object, due to movement of the object, to said attachment site;

with a mechanical component sensor, selected from the group consisting of force sensors and torque sensors, detecting, as a further sensed value, at least one value selected from the group consisting of a force value originating from said object and a torque value originating from said object; and providing said further sensed value from said mechanical component sensor to said control processor and, with said control processor, determining said force or torque originating from said object therefrom, and augmenting said control of said kinematic chain dependent on said force or torque originating from said object, so as to maintain said end effector in said spatial relation despite the movement of the object.

\* \* \* \* \*